United States Patent [19]

Karaki et al.

[11] Patent Number: 4,938,067
[45] Date of Patent: Jul. 3, 1990

[54] LOW TEMPERATURE ULTRASONIC MICROSCOPE

[75] Inventors: Koichi Karaki, Hino; Masahiro Aoki, Mizuho; Mitsugu Sakai; Yasuo Sasaki, both of Hachioji, all of Japan

[73] Assignee: Olympus Optical Co., Ltd., Tokyo, Japan

[21] Appl. No.: 336,477

[22] Filed: Apr. 12, 1989

[30] Foreign Application Priority Data

Apr. 14, 1988 [JP] Japan .................. 63-92201

[51] Int. Cl.⁵ ............................ G01N 29/00
[52] U.S. Cl. ................................ 73/606
[58] Field of Search ............ 73/644, 606, 607, 618, 73/619

[56] References Cited

FOREIGN PATENT DOCUMENTS 154961 6/1988 Japan .................. 73/606
154962 6/1988 Japan .................. 73/606

OTHER PUBLICATIONS

"Cryogenic Acoustic Microscopy", by J. Heiserman, D. Rugar and C. F. Quate; Edward L. Ginzton Laboratory, Standford University, Stanford, CA; J. Acoust. Soc. Am. 67(5), May 1980; 1980 Acoustical Society of America.

Primary Examiner—Jerry W. Myracle
Attorney, Agent, or Firm—Armstrong, Nikaido, Marmelstein, Kubovcik & Murray

[57] ABSTRACT

This low temperature ultrasonic microscope comprises an adiabatic container having an opening in the upper part and containing a low temperature liquid which is an ultrasonic wave transmitting medium, a sample supporting member supporting a sample to be observed, removably inserted into the adiabatic container through the opening and arranged at the upper end out of the adiabatic container, an ultrasonic wave image observing device which has an acoustic lens arranged within the adiabatic container and projecting an ultrasonic wave beam toward the sample, the above mentioned device detecting sound waves projected from the acoustic lens and disturbed by the sample and obtaining an ultrasonic wave image, a housing part housing the upper end part of the sample supporting member and a connecting member which can connect through a path the housing part and adiabatic container with each other.

9 Claims, 4 Drawing Sheets

LOW TEMPERATURE ULTRASONIC MICROSCOPE

BACKGROUND OF THE INVENTION

1. Field of the Invention

This invention relates to a low temperature ultrasonic microscope using such low temperature liquid as liquid nitrogen, liquid argon or liquid helium as an ultrasonic wave transmitting medium.

2. Related Art Statement

There is already practiced an ultrasonic microscope whereby a sample to be observed is two-dimensionally scanned with an ultrasonic wave beam and reflected waves or transmitted waves from the sample are received to form an ultrasonic wave image of the sample. In such ultrasonic microscope, in order to obtain more accurate picture image information from the sample, it is strongly required to elevate the resolution of the sample image to be higher.

The plane resolution of an ultrasonic microscope is determined by the wavelength of the sound wave in the ultrasonic wave transmitting medium. On the other hand, there is a relation of $c = f \cdot \lambda$ among the sound velocity $c$, frequency $f$ and wavelength $\lambda$ of the sound wave in the transmitting medium. Therefore, in order to elevate the resolution, that is, to make the wavelength of the sound wave small, it is considered to make the frequency $f$ of the sound wave large or to use a transmitting medium of a small sound velocity $c$. In a conventional ultrasonic microscope, as water has been used as an ultrasonic wave transmitting medium, in order to elevate the resolution, there has been used a method of elevating the frequency $f$ of the sound wave. However, as the absorption of the sound waves in the transmitting medium is proportional to the square of the frequency $f$ of the sound wave, there is a limit to the elevation of the frequency in practice. That is to say, in order to obtain a picture image of sufficient S/N, it is necessary to receive reflected waves above a certain level from the sample. Therefore, with the elevation of the frequency, it is necessary to shorten the distance for which the sound waves propagate through the transmitting medium and to reduce the attenuation caused by the absorption. This means to make small the working distance of an acoustic lens, that is, to make small the radius of curvature of the acoustic lens.

In the ultrasonic microscope practiced at present, there are obtained a frequency of 1.5 to 2.0 GHz and a resolution of 0.7 to 0.5 μm. The resolution on this level corresponds to the case of observing with an ordinary optical microscope of a lens radius of curvature of 50 to 30 μm and a working distance of about 30 to 10 μm. In order to realize a resolution above this level, it is necessary to make smaller the working distance of the lens. However, it is difficult in the precision in working the lens and in the use of the apparatus.

Thus, the resolution of the ultrasonic microscope using water as a transmitting medium has reached the same level as of the resolution of the optical microscope but, depending on the sample to be observed, in the case of observing such electronic device as, for example, a super LSI device or ceramic device, a resolution above that of the optical microscope is required and it is strongly required to develop an ultrasonic microscope of a higher resolution.

In order to attain this object, it is considered to use a transmitting medium lower in the sound velocity $c$ or absorption than water. Such transmitting medium is such low temperature liquid as liquid nitrogen, liquid argon or liquid helium. An ultrasonic microscope apparatus using this low temperature liquid as a transmitting medium is mentioned on pages 1629 to 1637 of The Journal of The Acoustic Society of America, Vol. 67 (1980). In this known ultrasonic microscope apparatus, a sample stand is arranged in the bottom of an adiabatic container, a sample is fitted on this sample stand and, on the other hand, an acoustic lens is arranged above the sample to two-dimensionally scan the sample.

However, the above described known ultrasonic microscope apparatus has it as an object to confirm the resolution and therefore has defects that it is very difficult to position the sample and it is difficult to replace the sample.

In order to cope with it, the present applicant has suggested an ultrasonic microscope wherein a sample rod supporting a sample is removably inserted into an adiabatic container containing such low temperature liquid as liquid nitrogen through a sliding seal and gate valve.

Now, in case such low temperature liquid as liquid nitrogen is used as a transmitting medium, this low temperature liquid will be usually in a boiling state under the atmospheric pressure. There is a problem that, due to bubbles produced by this boiling, a vibration will be generated and a picture image will be fogged. In order to prevent the picture image from being fogged, while the lens is being scanned to take in the picture image, the boiling of such low temperature liquid as liquid nitrogen may be stopped. Therefore, in order to stop the boiling of the low temperature liquid, it is considered to seal the adiabatic container during the scanning so that the internal pressure may be elevated by the boiling of the low temperature liquid itself and the boiling may be stopped.

However, this method has such defect as in the following. That is to say, the sample rod is fixed by the sliding seal which fixes the sample rod with only the friction of the sample rod with an O-ring and is not high in the rigidity. Therefore, by the elevation of the internal pressure of the adiabatic container, the sample rod will be pushed up though slightly and the distance between the lens and sample will vary. That is to say, the focus will be out.

In order to avoid it, it is considered to adjust a leak valve so that the evaporation amount after the boiling stops may escape and the pressure may be constant during the scanning. However, in this method, it is difficult to stably reproduce the same state with the boiled amount of the low temperature liquid, the amount of the liquid and the other factors. Therefore, the focus adjustment of a submicron order required of the low temperature ultrasonic microscope can not be stably made.

OBJECT AND SUMMARY OF THE INVENTION

An object of the present invention is to provide a low temperature ultrasonic microscope wherein it is easy to position and replace a sample and a stabilized focus adjustment can be made.

The low temperature ultrasonic microscope of the present invention comprises an adiabatic container having an opening in the upper part and containing a low temperature liquid which is an ultrasonic wave transmitting medium, a sample supporting member supporting a sample to be observed, removably inserted into the above mentioned adiabatic container through the above mentioned opening and arranged at the upper end out of the above mentioned adiabatic container, an ultrasonic wave image observing means which has an acoustic lens arranged within the above mentioned adiabatic container and projecting an ultrasonic wave beam toward the above mentioned sample, the above mentioned means detecting sound waves projected from the above mentioned acoustic lens and disturbed by the above mentioned sample and obtaining an ultrasonic wave image, a housing part housing the upper end part of the above mentioned sample supporting member and a connecting means capable of connecting through a path the above mentioned housing part and adiabatic container with each other.

The other features and advantages of the present invention will become apparent enough with the following explanation.

BRIEF DESCRIPTION OF THE DRAWINGS

FIG. 1 is a sectioned view showing the upper side of a low temperature ultrasonic microscope.

FIG. 2 is a sectioned view showing the lower side of the low temperature ultrasonic microscope.

FIG. 3 is an explanatory view showing the schematic formation of an ultrasonic wave image observing means.

DETAILED DESCRIPTION OF THE PREFERRED EMBODIMENTS

Figure 1:
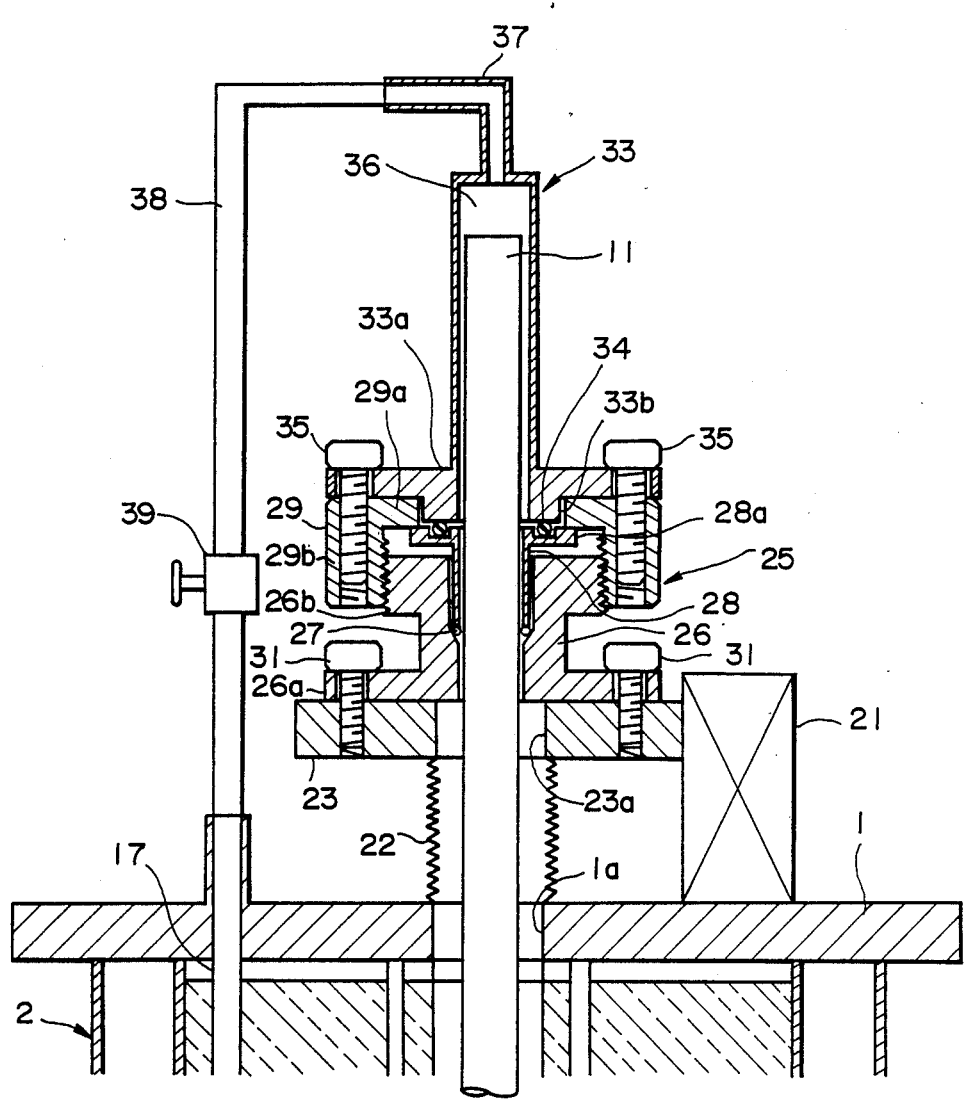
FIGS. 1 to 3 relate to the first embodiment of the present invention.
Figure 2:
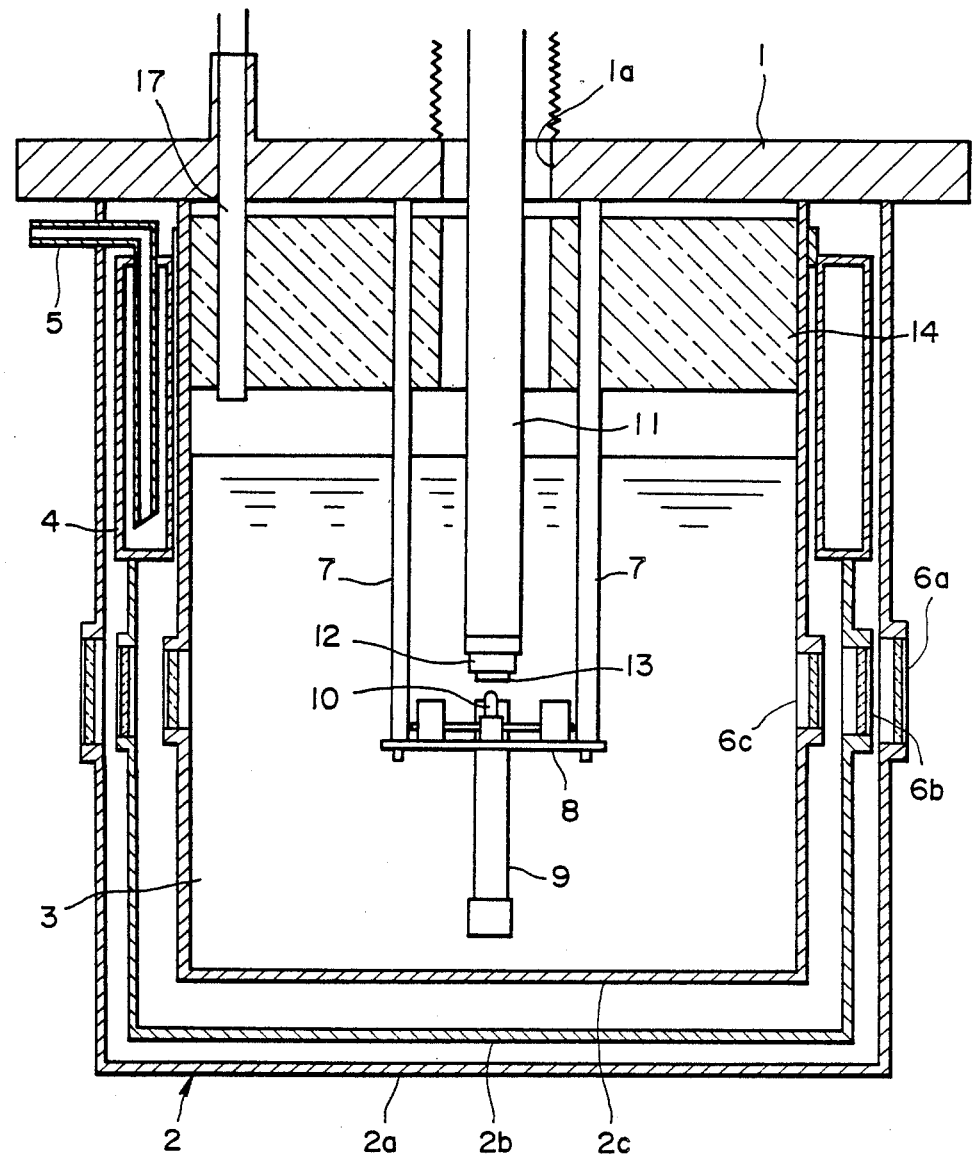
Figure 3:
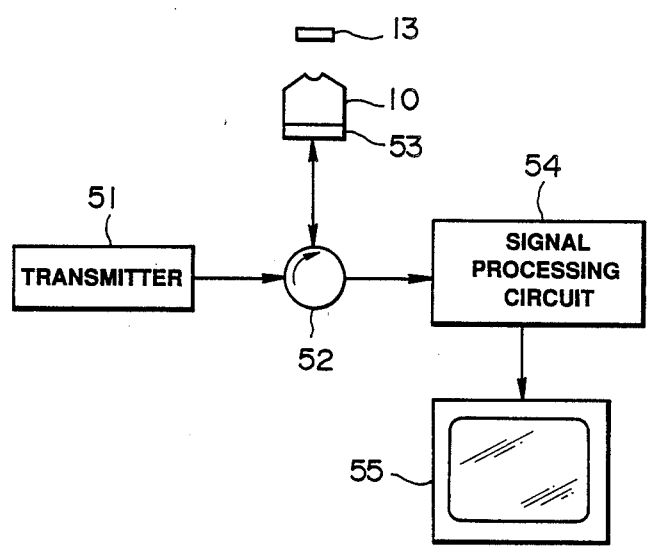

The first embodiment of the present invention is shown in FIGS. 1 to 3.

As shown in FIG. 2, the low temperature ultrasonic microscope of this embodiment has a base 1 below which a low temperature tank 2 as an adabatic container is sealed and fitted. Liquid nitrogen 3 which is an ultrasonic wave transmitting medium is contained in this low temperature tank 2 which is of a double vacuum structure of triple containers 2a, 2b and 2c and within which an annular tank 4 is provided. A pipe 5 is led into this annular tank 4 through the outside container 2a so that liquid nitrogen may be enclosed through this pipe 5. The temperature elevlating action from outside is to be prevented by the annular tank 4 enclosing this liquid nitrogen. The respective side walls of the containers 2a, 2b and 2c of the above mentioned low temperature tank 2 are provided respectively with peep holes 6a, 6b and 6c through which the distance between the acoustic lens and sample may be confirmed.

The above mentioned base 1 has an opening 1a in the central part. Four stays 7 are provided to project downward on the lower surface of the base 1 around this opening 1a. By the way, in FIG. 2, only two stays 7 are shown. A scanner supporting stand 8 is fitted to the lower ends of these stays 7 and is fitted with an xy scanner 9 to which an acoustic lens 10 is fitted. This acoustic lens 10 is to be two-dimensionally driven in an xy plane intersecting at right angles with the paper surface by the above mentioned xy scanner 9.

A sample rod 11 is inserted into the above mentioned low temperature tank 2 through the opening 1a of the above mentioned base 1 and is arranged in the z direction upward of the above mentioned acoustic lens 10. A sample stand 12 is fitted to the lower end of this sample rod 11 and is to be fitted with a sample 13 to be observed. As shown in FIG. 3, the high frequency electric power generated from a transmitter 51 is converted to ultrasonic waves by a piezoelectric transducer 53 bonded to the acoustic lens 10 through a circulator. These ultrasonic waves are converged by the above mentioned acoustic lens 10 and the ultrasonic wave beam emitted from this acoustic lens 10 reaches a sample 13 through liquid nitrogen 3 which is a transmitting medium. Therefore, the ultrasonic wave beam will be two-dimensionally scanned by the ultrasonic wave beam. The reflected waves from the sample 13 are concentrated by the above mentioned acoustic lens 10, are converted to an electric signal by the above mentioned piezoelectric transducer 53 and this electric signal is converted to a picture image signal by a signal processing circuit 54 through the above mentioned circulator 52. This picture image signal is input into a monitor 55 in which an ultrasonic wave image is displayed.

By the way, the above mentioned sample rod 11 is formed of a hollow pipe, for example, of SUS. If the above mentioned sample rod 11 is formed of a material of the same thermal expansion coefficient as of the stay 7, even if the liquid level of the liquid nitrogen 3 varies, the sample 13 will be able to be prevented from being displaced in the z direction with respect to the acoustic lens 10. An annular adiabatic member 14 is arranged near the opening of the above mentioned low temperature tank 2 to attain the adiabatic effect on the opening side.

A pipe 17 passing through the base 1 is fitted to the above mentioned base 1 and is led on the lower end side into the above mentioned low temperature tank 2 through the above mentioned adiabatic member 14.

On the other hand, as shown in FIG. 1, an X-Y-Z stage 21 for moving the above mentioned sample rod 11 in X, Y and Z directions is fitted on the above mentioned base 1 and a bellows 22 through which the above mentioned sample rod 11 is inserted is fitted on the upper surface of the base 1 around the opening 1a of the above mentioned base 1. A movable table 23 of the above mentioned X-Y-Z stage 21 is fitted to the upper end of this bellows 22 and has a hole 23a through which the above mentioned sample rod 11 is inserted.

A sliding seal 25 formed of a holding sleeve 26, O-ring 27, sleeve 28 and cap member 29 is fitted on the upper surface of the above mentioned movable table 23 so as to airtightly seal the low temperature tank 2 and outside part and to fix the above mentioned sample rod 11. The above mentioned holding sleeve 26 has a hollow part which is of an inside diameter somewhat larger than the outside diameter of the above mentioned sample rod 11 and through which the above mentioned sample rod 11 is inserted and has a lower flange 26a and upper flange 26b respectively at the lower end and upper end. The above mentioned lower flange 26a is fixed on the above mentioned movable table 23 with screws 31. A male screw is formed on the outer periphery of the above mentioned upper flange 26b. The hollow part of the above mentioned holding sleeve 26 is made larger in the inside diameter from the upper end to the substantial middle so as to form an annular space from the outer periphery of the sample rod 11. The above mentioned O-ring 17 and cylindrical sleeve 28 are fitted in turn in this annular space. A flange 28a projecting from the upper end of the above mentioned holding sleeve 28 is formed at the upper end of the above mentioned sleeve 28 and has an annular groove formed on the upper end surface. The above mentioned cap member 29 has a disc part 29a having a hollow part through which the above mentioned sample rod 11 is inserted and a cylindrical part 29b extended downward from the outer periphery of this disc part 29a. A female screw screwed with the male screw formed on the outer periphery of the upper flange 26b of the above mentioned holding sleeve 26 is formed on the inner periphery of the above mentioned cylindrical part 29b. The above mentioned disc part 29a contacts on the lower end surface with the upper end surface of the flange 28a of the above mentioned sleeve 28. When the above mentioned cap member 29 is screwed to the above mentioned holding sleeve 26 and is fastened, the low temperature tank 2 will be kept airtight from outside.

In this embodiment, an airtight cap 33 housing the upper end side of the above mentioned sample rod 11 and forming an upper space 36 is provided, is formed to be a cylinder closed at the upper end, has a flange 33a formed at the lower end, has a projection 33b to be inserted into the hollow part of the disc part 29a of the above mentioned cap member 29 further formed at the lower end and is fixed on the upper end surface of the above mentioned cap member 29 with screws 35. An O-ring 34 is fitted in the groove formed on the upper end surface of the flange 28a of the above mentioned sleeve 28 so that the above mentioned projection 33b may contact this O-ring 34. The upper space 36 within the above mentioned airtight cap 33 is airtightly sealed by this O-ring 34. A pipe 37 communicating with the above mentioned upper space 36 is provided at the upper end of the above mentioned airtight cap 33 and is connected with the pipe 17 fitted to the above mentioned base 1 through a hose (or pipe) 38 provided with a valve 39 in the course so that the above mentioned upper space 36 may communicate with the above mentioned low temperature tank 2 through this hose 38.

The using manner and operation of this embodiment formed as in the above shall be explained in the following.

First of all, in observing the sample 13, the sample rod 11 fitted with the sample 13 is inserted into the low temperature tank 2 through the opening 1a of the base 1 and is fixed to the above mentioned sliding seal 25. In this case, the valve 39 will be closed. Then the airtight cap 33 is fitted to the cap member 29 of the sliding seal 25 with the screws 35 so that the upper space 36 may be sealed with the O-ring 34. When the above mentioned valve 39 is opened, the above mentioned upper space 36 will communicate with the low temperature tank 2 and will be of the same pressure as the internal pressure of the low temperature tank 2. Therefore, the sample rod 11 will be subjected to equal pressures in the vertical direction and will not move vertically. That is to say, the focus will not be out.

By the way, in observing the sample, the sample rod 11 is moved in the X, Y and Z directions by the X-Y-Z stage 21 to adjust the focus.

In taking out the sample rod 11 to replace the sample or the like, the above described operation is made in the reverse order. That is to say, first the valve 39 is closed and the low temperature tank 2 and upper space 36 are separated from each other. Then, the screws 35 are removed and the airtight cap 33 is dismounted.

Thus, according to this embodiment, as the sample rod 11 supporting the sample 13 is removably inserted into the low temperature tank 2, it is easy to position and replace the sample 13. Further, as the low temperature tank 2 housing the lower end of the sample rod 11 and the upper space housing the upper end of the sample rod 11 are made to communicate with each other, even if the pressure within the low temperature tank 2 varies, the sample rod 11 will not vertically move and the focus will be able to be stably adjusted.

Figure 4:
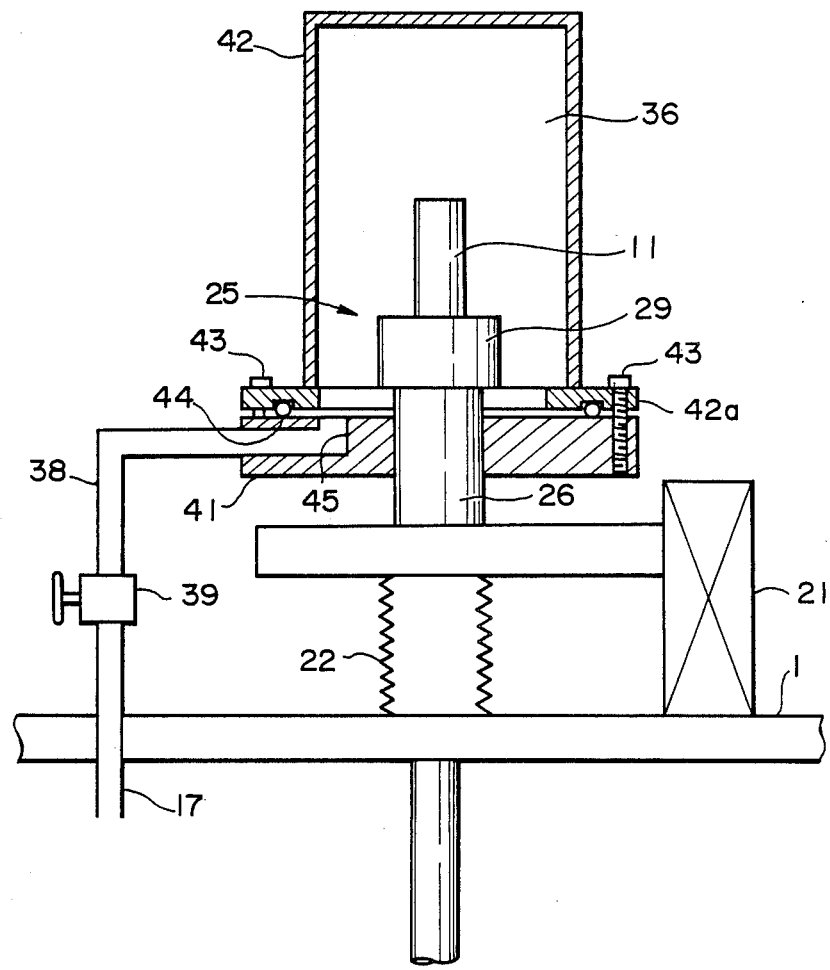
FIG. 4 is a sectioned view showing the upper side of a low temperature ultrasonic microscope of the second embodiment of the present invention.

The second embodiment of the present invention is shown in FIG. 4.

In the first embodiment, the airtight cap 33 is sealed with the O-ring 34 and is fitted to the cap member 28 so as to be as small as possible but, in this embodiment, without considering so much to make it small, the entire sliding seal is airtightly covered with the airtight cap.

In this embodiment, a flange 41 is fitted to the holding sleeve 26, an airtight cap 42 covering the upper end side of the sample rod 11 is fitted on this flange 41 and a flange 42a is formed at the lower end of this airtight cap 42 and is fixed on the upper surface of the above mentioned flange 41 with screws 43. An O-ring 44 is interposed between the above mentioned flange 42a and flange 41 so as to seal the upper space 36.

A path 45 connecting the above mentioned upper space 36 with the outside is formed in the above mentioned flange 41 and is connected with the pipe 17 inserted into the low temperature tank 2 through the hose 38 in which the valve 39 is interposed.

By the way, the hose 38 may be connected directly with the above mentioned airtight cap 42.

Also, the above mentioned airtight cap 42 may be formed of such flexible material as plastic or rubber.

The other formations, operations and effects are the same as in the first embodiment.

By the way, the present invention is not limited to the above mentioned respective embodiments but can be applied, for example, to a transmitting type ultrasonic microscope wherein ultrasonic waves having passed through the sample while dispersing and attenuating are received to be made a picture image.

As explained above, according to the present invention, there are effects that, as the sample rod supporting the sample (sample supporting member) is removably inserted into the adiabatic container containing the low temperature liquid, it is easy to position and replace the sample and further, as the adiabatic container housing the lower end of the sample rod and the upper space housing the upper end are connected with each other, even if the pressure within the adiabatic container varies, the sample rod will not vertically move and the focus will be able to be stably adjusted.

It is apparent that, in this invention, working modes different in a wide range can be formed on the basis of this invention without departing from the spirit and scope of the invention. This invention is not restricted by its specific working modes except being limited by the appended claims.

What is claimed is:

1. A low temperature ultrasonic microscope comprising:
    an adibatic container having an opening in the upper part and containing a low temperature liquid which is an ultrasonic wave transmitting medium;
    a sample supporting member supporting a sample to be observed, removably inserted into said adiabatic container through said opening and arranged at the upper end out of said adiabatic container;

an ultrasonic wave image observing means which has an acoustic lens arranged within said adiabatic container and projecting an ultrasonic wave beam toward said sample, said means detecting sound waves projected from said acoustic lens and disturbed by said sample and obtaining an ultrasonic wave image;

a housing part housing the upper end part of said sample supporting member; and a connecting means capable of connecting through a path said housing part and adiabatic container with each other.

2. A low temperature ultrasonic microscope according to claim 1 further comprising a sealing means sealing said opening of said adiabatic container when said sample supporting member is inserted in said adiabatic container.

3. A low temperature ultrasonic microscope according to claim 2 wherein said housing part is removably provided for said sealing means above said sealing means.

4. A low temperature ultrasonic microscope according to claim 2 wherein said housing part is removably provided for said sealing means holding part so as to cover said sealing means.

5. A low temperature ultrasonic microscope according to claim 2 wherein said sealing means is also said sample supporting member fixing means.

6. A low temperature ultrasonic microscope according to claim 1 wherein said sample supporting member is rod-like.

7. A low temperature ultrasonic microscope according to claim 1 wherein said connecting means is a tubular member connected at one end to said housing part and at the other end to said adiabatic container.

8. A low temperature ultrasonic microscope according to claim 7 wherein said tubular member is provided in the course with a valve.

9. A low temperature ultrasonic microscope according to claim 1 wherein said acoustic lens projects an ultrasonic wave beam to said sample and also receives sound waves disturbed by said sample.

* * * * *